Figure 1:
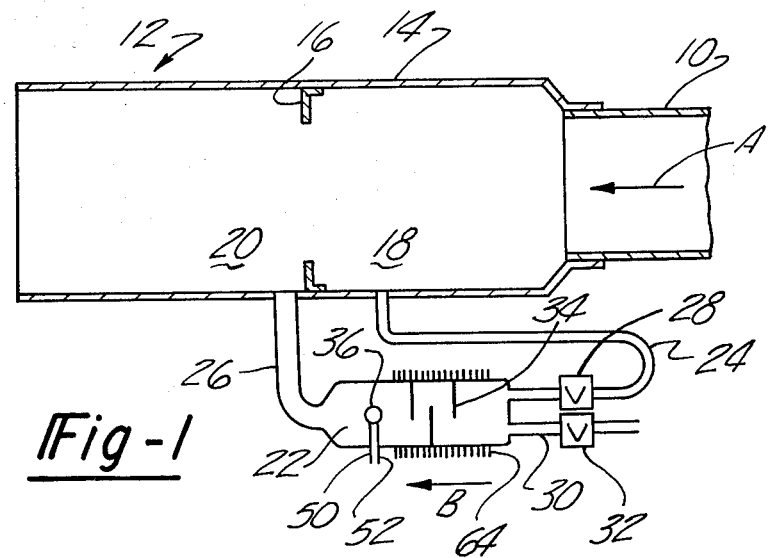

United States Patent [19]

Hadden et al.

[11] 3,965,749

[45] June 29, 1976

[54] SAMPLING AND DILUTION METHOD

[75] Inventors: Stephen C. Hadden, Cambridge; Leonard R. Hulls, Marblehead, both of Mass.

[73] Assignee: The United States of America as represented by the Secretary of the Army, Washington, D.C.

[22] Filed: Mar. 19, 1975

[21] Appl. No.: 559,856

[52] U.S. Cl............................................. 73/421.5 R
[51] Int. Cl.².......................................... G01N 1/22
[58] Field of Search.............................. 73/421.5 R

[56] References Cited
UNITED STATES PATENTS

| | | | |
|---|---|---|---|
| 2,013,998 | 9/1935 | Goldsborough | 73/421 R |
| 3,461,727 | 8/1969 | Everhard et al. | 43/421.5 |

*Primary Examiner*—S. Clement Swisher
*Attorney, Agent, or Firm*—Peter A. Taucher; John E. McRae; Nathan Edelberg

[57] ABSTRACT

A conduit arrangement for measuring unburned combustibles in the exhaust stream issuing from an engine. A restriction is provided in the exhaust duct to form a superatmospheric pressure zone upstream from the restriction and a subatmospheric pressure zone downstream from the restriction. A minor fraction of the exhaust gas is bypassed around the restriction through a conduit system communicating with the two above-mentioned zones. A sampling chamber containing a combustibles sensor is located in the conduit system. An auxiliary conduit communicates the interior of the sampling chamber with the ambient atmosphere so that cooling air is drawn into the chamber to dilute the sampled gas. The dilution air lowers the temperature of the gas-air mixture, thereby cooling the sensor against heat degradation by the otherwise undiluted gas. The dilution air also contributes oxygen to the gas stream, thereby enhancing catalytic oxidation processes on which certain sensors depend for response to combustibles (CO and CH).

1 Claim, 3 Drawing Figures

SAMPLING AND DILUTION METHOD

BACKGROUND AND SUMMARY OF THE INVENTION

It is known to position a semi-conductor such as tin oxide in a gaseous stream to detect combustibles such as carbon monoxide and/or hydrocarbons. An assumed operating mode of an "oxidizing" type semi-conductor sensor involves the adsorption of oxygen on the porous sensor surface to determine the sensor's electrical conductivity by affecting the population of electrons in the semi-conductor's conduction band; the oxygen weakly holds electrons which would otherwise be available in the conduction population. When the oxygen is surrendered to combustible gases it frees electrons for conduction, reducing the resistance of the sensor and increasing current flow therethrough.

For best operation and reasonable service life the semi-conductor materials known to applicant should be maintained in a temperature range between about 200°F and 300°F. Unfortunately engine exhaust temperatures are usually higher than this range. Therefore the exhaust gases should be cooled before passage across the semi-conductor bead. Cooling of the gases is also required or beneficial when using other types of sensors, such as electrochemical sensors (electrolysis of copper from copper borofluoxide electrolyte), infrared sensors, or spectrometric sensors.

The present invention deals with a conduit arrangement for cooling an engine exhaust gas sample before its passage over a combustibles sensor. The arrangement contemplates mechanism for diverting a minor fraction of the hot gas from the exhaust duct into a mixing chamber that communicates with a source of cooling air (such as the ambient atmospheric). The gas-air mixture is passed over the sensor to provide the readout.

Motive force for moving the diverted gas and coolant is provided by a restriction in the engine exhaust duct. Such restriction forms a superatmospheric pressure zone at an upstream location, and a subatmospheric pressure zone at a downstream location. The aforementioned mixing chamber communicates with the two zones so that the pressure differential (between the two zones) produces gas flow through the chamber. Coolant air flow is produced by the inductive effect of the subatmospheric pressure zone on the ambient. The arrangement uses no moving parts, with the possible exception of certain control valves that might prove necessary or desirable in some instances.

THE DRAWINGS

Figure 2:
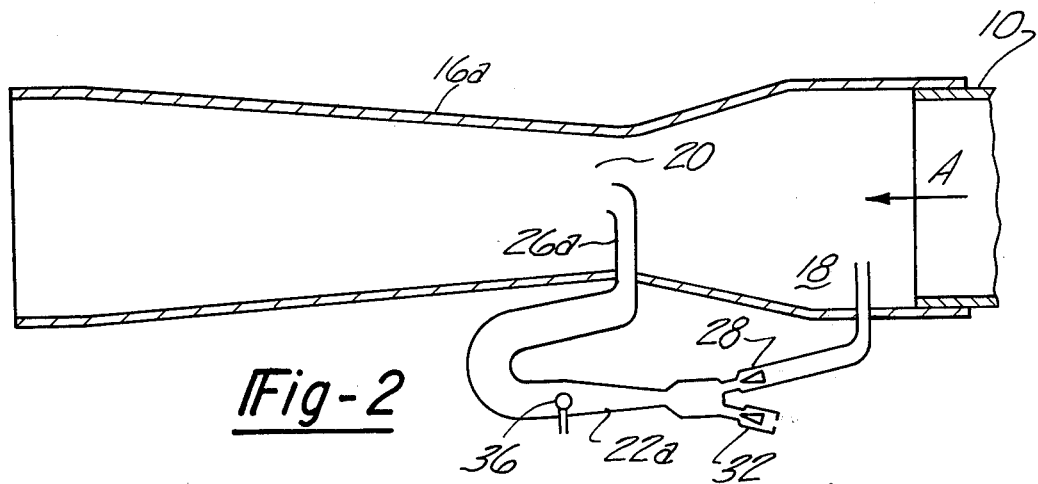

FIGS. 1 and 2 schematically illustrative two separate embodiments of the invention.

Figure 3:
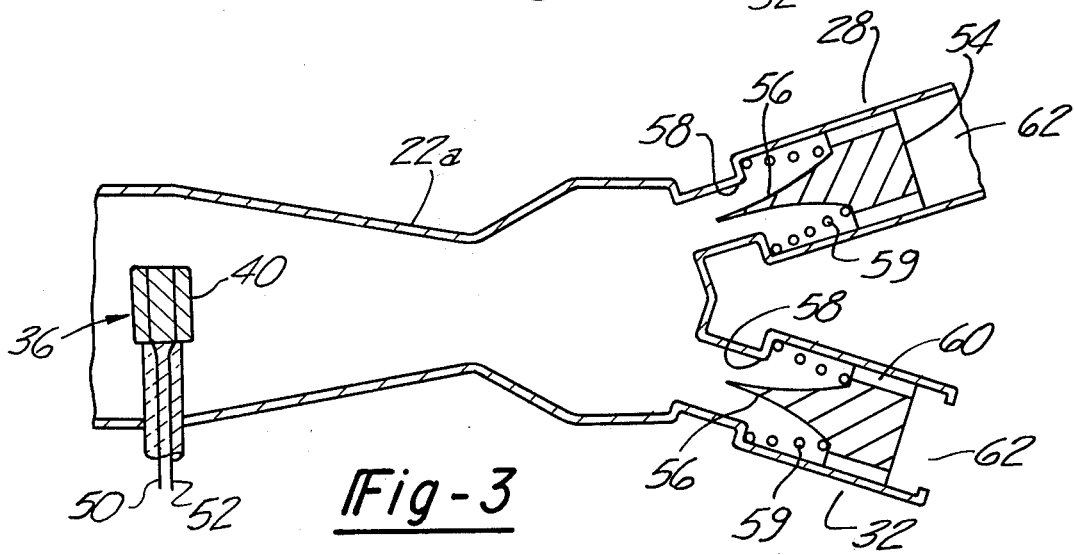

FIG. 3 fragmentarily illustrates a portion of the mechanism shown in FIG. 2.

Referring to FIG. 1, there is fragmentarily shown the tailpipe area 10 of an exhaust duct for a non-illustrated engine used as an automotive propulsion mechanism (auto, truck, bus, etc.). Flow of hot exhaust gas is in the direction of arrow A.

The illustrated tailpipe is fitted with an add-on measuring device 12 for measuring combustibles in the hot gas stream issuing from the pipe. Device 12 comprises a flow tube 14 having a larger diameter than duct 10. Fixedly located within tube 14 is an orifice plate 16 defining an upstream zone 18 at superatmospheric pressure and a downstream zone 20 at a slightly negative subatmospheric pressure. The orifice defined by plate 16 has a diameter approximately the same as that of duct 10 so that plate 16 has minimal restrictive effect on gas flow through the exhaust system.

The pressure differential between zones 18 and 20 is used as a motive force to move hot gases through a gas sampling chamber 22 in the arrow B direction. As shown in FIG. 1, chamber 22 communicates with superatmospheric pressure zone 18 via a conduit 24; chamber 22 communicates with subatmospheric pressure zone 20 via a conduit 26. Conduit 26 has a diameter somewhat larger than conduit 24 to increase the inductive force and overcome flow resistance in the sampling system defined by passage members 24, 22 and 26. Conduit 24 may be provided with a conventional constant flow valve 28 constructed in the general fashion shown in FIG. 3.

Chamber 22 communicates with the ambient atmosphere via a third conduit 30 containing a conventional constant flow valve 32 similar to the corresponding valve shown in FIG. 3. Valves 28 and 32 respond to varying pressure differentials thereacross to maintain constant flows in the respctive conduits. The valves are intended to cooperatively maintain a certain dilution ratio (gas versus air) in spite of variations in engine operation, e.g. load and/or r.p.m.

The negative pressure condition at zone 20 provides the motive force for inducing flow of ambient air through conduit 30 into chamber 22. Baffles 34 may be located within the chamber to promote mixture of the gas and air streams, and to exert inertial separation effects on any soot particles entrained in the gas. The gas-air mixture passing through baffles 34 encounters a conventional combustibles sensor 36 which may be constructed similarly to sensors marketed by Figaro Engineering Inc. of Japan, its model 109 (high temperature mode) or model 105 (low temperature mode). Operable sensors are believed to be shown and described in such U.S. Pat. Nos. as 3,631,436 and 3,625,756. Such sensors may take the form of porous semi-conductor beads 40 (see FIG. 3) operatively connected to electrical lead wires 50 and 52 extending across a voltage source, not shown. A meter may be connected in the circuit to measure the bead resistance. Bead 40 performance (combustibles measurement accuracy) is dependent on the quantity of air drawn into chamber 22 through conduit 30 in relation to the quantity of hot gas drawn into the chamber through conduit 24. The flow quantities may be individually maintained at preselected values by means of conventional flow valves 28 and 32, shown schematically in FIG. 3. As seen in FIG. 3, each valve comprises a floating piston 54 having a contoured surface 56 adapted to progressively restrict the intervening flow space between surfaces 56 and 58 during movement of the piston by the pressure differential thereacross; the flow rate is determined by the spring rate and load of spring 59. The piston side surface may be fluted, as at 60, to provide adequate flow area from upstream space 62. If the engine is run at a known load and r.p.m. it may not be necessary to use constant flow valves 28 and 32. Such valves are employed to compensate for variations in engine operating conditions.

The coolant effect of the air on the gas is determined by the flow ratings of valves 28 and 32 or the sizes of conduits 24 and 30 (if the valves are not used). Coolant flow is selected according to the preferring operating temperature of the sensor bead 40, which may be on the order of 200°F - 300°F. The cooling effect of the air may be augmented by other devices such as heat transfer fins 64 (FIG. 1) or a water jacket, now shown.

The use of direct air cooling, i.e. mixing the hot gases with relatively cool air has an advantage over other cooling methods in that the air furnishes oxygen which promotes catalytic oxidation on the bead 40 surface. The diluting effect of the air also minimizes saturation effects from combustibles and humidity, as well as reducing the quantity of particulates moved across the bead surface over prolonged time periods, thereby minimizing the tendency of the particulates to clog or coat the bead surface as would degrade its response. Baffles 34 cooperate with the dilution effect by separating some particulates from the stream before they are able to reach the bead.

The device shown in FIGS. 2 and 3 is essentially the same as the FIG. 1 device. However in the FIG. 2 arrangement the restriction in the exhaust duct is formed by a venturi 16a rather than an orifice plate, and the sampling chamber 22a is given a venturi shape to promote intermixture of the gas and air streams. Performance of the FIG. 2 device is similar to that of the FIG. 1 device.

The principal advantage of the invention is the absence of moving parts (other than valves 28 and 32). This is distinguished from a fan or pump heretofore employed for gas sampling purposes. If desired, the zone of negative pressure (e.g. zone 20) could be provided by the engine's inlet manifold. In that event conduit 24 would be connected to the engine exhaust duct, and conduit 26 would be connected to the inlet manifold; the restriction (orifice plate of venturi 16a) would not be employed.

We wish it to be understood that we do not desire to be limited to the exact details of construction shown and described for obvious modifications will occur to a person skilled in the art.

We claim:

1. Means for measuring combustibles passing through the exhaust duct of an engine: said measuring means comprising a restriction in the exhaust duct forming a first superatmospheric pressure zone upstream therefrom and a second subatmospheric pressure zone downstream therefrom; a sampling chamber having a first conduit communicating with the superatmospheric pressure zone and a second conduit communicating with the subatmospheric pressure zone; said sampling chamber and its conduits being constructed to offer a flow resistance such that some of the engine exhaust gas is caused to be temporarily diverted through the sampling chamber via the first and second conduits; a third air coolant conduit communicating with the ambient atmosphere with the sampling chamber, whereby cooling air is drawn into said chamber for intermixture with the diverted gas; and a combustibles sensor located within the chamber for detecting combustibles in the flowing gas-air mixture; a first pressure-responsive constant flow valve located in the first conduit, and a second pressure-responsive constant flow valve located in the third conduit; said valves cooperatively assuring a substantially constant ratio between the flow rates in the first and third conduits irrespective of variations in pressure differential between the first and second zones.

* * * * *